United States Patent
Yuk et al.

(10) Patent No.: US 10,982,250 B2
(45) Date of Patent: Apr. 20, 2021

(54) METHODS OF PROTEIN PRODUCTION

(75) Inventors: Inn Huam Yuk, Berkeley, CA (US); Bradley Richard Snedecor, Portola Valley, CA (US); Dana Christian Andersen, Menlo Park, CA (US)

(73) Assignee: Genentech, Inc., South San Francisco, CA (US)

( * ) Notice: Subject to any disclaimer, the term of this patent is extended or adjusted under 35 U.S.C. 154(b) by 1130 days.

(21) Appl. No.: 12/441,775

(22) PCT Filed: Sep. 17, 2007

(86) PCT No.: PCT/US2007/078644
§ 371 (c)(1),
(2), (4) Date: Nov. 2, 2009

(87) PCT Pub. No.: WO2008/036600
PCT Pub. Date: Mar. 27, 2008

(65) Prior Publication Data
US 2010/0256336 A1 Oct. 7, 2010

Related U.S. Application Data

(60) Provisional application No. 60/826,020, filed on Sep. 18, 2006.

(51) Int. Cl.
*C12P 21/00* (2006.01)

(52) U.S. Cl.
CPC .................................. *C12P 21/005* (2013.01)

(58) Field of Classification Search
None
See application file for complete search history.

(56) References Cited

U.S. PATENT DOCUMENTS

| | | | | |
|---|---|---|---|---|
| 5,318,898 A | * | 6/1994 | Israel ....................... | C12N 1/38 435/69.1 |
| 5,856,179 A | * | 1/1999 | Chen ..................... | C12N 5/0018 435/325 |
| 7,429,491 B2 | * | 9/2008 | Luan ..................... | C12N 5/0018 435/404 |

FOREIGN PATENT DOCUMENTS

| WO | WO2006/026759 | * | 3/2006 |
|---|---|---|---|
| WO | WO 2006026759 | | 3/2006 |

OTHER PUBLICATIONS

Harris (Dev. Biol. 122: 117-127 (2005); abstract).*
Kennedy et al. (Clin. Exp. Immunol. 98:245-251 (1994)).*
Wright et al (Springer Semin Immunopathology ,15 :259-273 (1993)).*
Delente (Trends in Biotechnology 3, letters to editor, No. 9, (1985)).*
Olden et al (Biochem et Biophys Acta 650:209-232 (1982)).*
Kennedy et al. (Clin. Exp. Immunol. 98:245-251; cited on IDS filed Oct. 5, 2009).*
Gorfien et al. (BioPharm International, Apr. 2003, pp. 34-40) (Year: 2003).*
Zhang et al (Anal. Chem. 2008, 80, 2379-2390) cited on IDS filed Jun. 22, 2015, (Year: 2008).*
Yuk et al. (Biotechnology and Bioengineering, vol. 108, No. 11, Nov. 2011) cited on IDS filed Jun. 22, 2015 (Year: 2011).*
Lee et al (Feb. 2005, Biotechnol. Prog. vol. 21, pp. 134-139) (Year: 2005).*
Hayter et al (1992, Biotechnology and Bioengineering, vol. 39, pp. 327-335) (Year: 1992).*
Ahmed, "Advanced glycation endproducts—role in pathology of diabetic complications", Diabetes Research and Clinical Practice; 67: 3-21, (2005).
Cai, et al., "Advanced glycation end product (AGE) receptor 1 suppresses cell oxidant stress and activation signaling via EGF receptor", PNAS, vol. 103, No. 37, 13801-13806, (2006).
Franke, et al., "Increased levels of advanced glycation end products in human cataractous lenses", Journal of Cataract Surg., 29: 998-1004, (2003).
Harris, et al., "Heterogeneity of recombinant antibodies: linking structure to function", Analytical Chemistry Department, vol. 122, pp. 117-127, (2005).
Vrdoljak, et al., "In vitro glycation of human immunoglobulin G", Clinica Chimica Acta, vol. 345, pp. 105-111, (2004).
Yak, et al., "Controlling Glycation of Recombinant Antibody in Fed-Batch Cell Cultures", *Biotechnology and Bioengineering*, Nov. 2011, vol. 108, No. 11, pp. 2600-2610.
Zhang, et al., "Unveiling a Glycation Hot Spot in a Recombinant Humanized Monoclonal Antibody", *Anal. Chem.* 2008, vol. 80, pp. 2379-2390.

* cited by examiner

*Primary Examiner* — Meera Natarajan
(74) *Attorney, Agent, or Firm* — Baker Botts L.L.P.

(57) ABSTRACT

A method of reducing glycation of an amino acid in a protein produced by a host cell in cell culture medium is disclosed.

20 Claims, 7 Drawing Sheets

Specification includes a Sequence Listing.

METHODS OF PROTEIN PRODUCTION

The present application is a non-provisional application filed under 37 CFR § 1.53(b), claiming benefit under 35 USC § 119(e) of U.S. Provisional Application Ser. No. 60/826,020, filed 18 Sep. 2006, the entire contents of which is hereby incorporated by reference.

INCORPORATION OF SEQUENCE LISTING

This application includes a Sequence Listing submitted via EFS-Web as a computer readable form 4,002 byte file entitled "GNE030US.txt" created on Apr. 6, 2010, which is hereby incorporated herein by reference in its entirety.

FIELD OF THE INVENTION

A method of reducing glycation of an amino acid in a protein produced by a host cell in cell culture medium is disclosed.

BACKGROUND

Glycation is a common post-translational modification of proteins, resulting from the chemical reaction between reducing sugars such as glucose and the primary amino groups on protein (Ahmed, N., Diabetes Res. Clin. Practice 67:3-21 (2005)). The first step in this non-enzymatic glycosylation reaction is a nucleophilic addition reaction between the open chain form of the reducing sugar and the free amino group on the protein (Ahmed, N., 2005, supra). The resulting aldimine (a reversible Schiff base) can undergo Amadori rearrangement to form a more stable ketoamine.

In vivo, glycated proteins can further undergo subsequent slow reactions, such as rearrangement, oxidation, dehydration, and polymerization, to form a host of heterogeneous species collectively termed as advanced glycation endproducts (AGEs). AGEs have been implicated in aging-related diseases and long-term diabetic complications: the formation and accumulation of AGEs in various tissues have been known to progress during normal aging and at an extremely accelerated rate in diabetes mellitus (Ahmed, N., 2005, supra; Cai, W. et al. Proc. Natl. Acad. Sci. USA, 103:13801-13806 (2006)). For instance, Nε-(Carboxymethyl)lysine (CML) is a well-characterized AGE (FIG. 1) that has demonstrated diabetic and age-dependent accumulation in the human lens and is associated with cataract formation (Sybille, F. et al., J. Cataract Refract. Surg. 29:998-1004 (2003)).

Glycation generates structural heterogeneity in recombinant polypeptides secreted from a host cell expressing the polypeptide during cell culture, such as during expression of the polypeptide during fermentation. For example, such heterogeneity was shown in the production of recombinant antibodies produced by cell culture processes (Harris, R. J., Dev Biol (Basel) 122: 117-127 (2005)). Because of the desirability of structural homogeneity of recombinant polypeptides, such as polypeptides used for biopharmaceuticals, there is a need to reduce the level of glycation of such polypeptides produced in cell culture.

SUMMARY OF THE INVENTION

The present invention relates to a method for producing a polypeptide, the method comprising culturing host cells expressing the protein in a cell culture medium comprising at least one reducing sugar in which the total reducing sugar concentration is maintained at 5 g/L or less for the majority of the cultivation time during protein production by either continuous reducing sugar feed or continuous nutrient feed (containing reducing sugar), operated semi-continuously or fully-continuously, and harvesting the protein from the cell culture, wherein glycation of the polypeptide is 70% or less of the glycation of the polypeptide produced by a control method. The continuous feed described herein pertains to either a reducing sugar feed or a nutrient supplement feed that contains reducing sugar, and this feed may be operated in semi-continuous or fully continuous mode.

According to an embodiment of the invention the polypeptide expressed by the host cell may be a naturally occurring peptide or a recombinant polypeptide expressed from a gene encoding such polypeptide and introduced into the host cell. The polypeptide may be a single polypeptide of interest or a mixture of polypeptide. In one embodiment, the polypeptide is an antibody, immunoglobulin, bispecific antibody, or antigen binding fragment thereof. Where the polypeptide is a mixture, the level of glycation and its reduction may be determined for one or more or all of the polypeptides.

In one embodiment, the method comprises maintaining the concentration of reducing sugar in the cell culture process at alternatively 4 g/L or less, at 3 g/L or less, at 2 g/L or less, or at 1 g/L or less.

In one embodiment, the reducing sugar is any reducing sugar or a mixture of more than one reducing sugars. A reducing sugar is a sugar comprising an aldehyde or ketone group in its structure, where the aldehyde or ketone may in equilibrium with a ring structure of the sugar. Such sugars were named for their property of reducing various inorganic ions, such as cupric ion to cuprous ion. In one embodiment, the reducing sugar is glucose. In one embodiment, the reducing sugar is any one or more of glucose, fructose, galactose, ribose, and deoxyribose. A reducing sugar or mixture of reducing sugars, according to one embodiment, may be mono-, di-, or polypsaccharide comprising a reducing sugar, such as a reducing sugar at an end of di- or polysaccharide chain which is capable of reacting with an amino acid side chain of a polypeptide in a glycation reaction.

In one embodiment, the method comprises maintaining the host cells in the cell culture without further providing (or feeding) reducing sugar to the cell culture for a period of time prior to harvesting the polypeptide from the cell culture, wherein the time prior to the harvesting is alternatively 72 hours or less, 48 hours or less, 36 hours or less, 24 hours or less, 12 hours or less, 6 hours or less, or 3 hours or less. The cessation of providing reducing sugar alternatively may occur by stopping the continuous feed process or by maintaining a continuous feed of nutrients lacking a reducing sugar.

In one embodiment, the method comprises contacting the host cells with an inoculation medium lacking a reducing sugar prior to the culturing of host cells expressing the polypeptide.

In one embodiment, the method comprises contacting the host cells with a batch feed medium lacking a reducing sugar after contacting with an inoculation medium and before the culturing of host cells expressing the polypeptide. In one embodiment, either, neither, or both of the inoculation medium and the batch feed medium lack a reducing sugar.

In one embodiment of the method, after the continuous feed, the cells are maintained in a cell culture medium without further addition of reducing sugar for a period of time before the harvesting, wherein the period of time is 72 hours or less, 48 hours or less, 36 hours or less, 24 hours or less, 12 hours or less, 6 hours or less, or 3 hours or less.

In one embodiment, the method comprises contacting the host cells with an inoculation medium lacking a reducing sugar prior to the culturing of host cells expressing the polypeptide and, after the continuous feed, the cells are maintained in a cell culture medium without further addition of reducing sugar for a period of time before the harvesting, wherein the period of time is 72 hours or less, 48 hours or less, 36 hours or less, 24 hours or less, 12 hours or less, 6 hours or less, or 3 hours or less.

In one embodiment, the method comprises contacting the host cells with a batch feed medium lacking a reducing sugar after contacting with an inoculation medium and before the culturing of host cells expressing the polypeptide and, after the continuous feed, the cells are maintained in a cell culture medium without further addition of reducing sugar for a period of time before the harvesting, wherein the period of time is 72 hours or less, 48 hours or less, 36 hours or less, 24 hours or less, 12 hours or less, 6 hours or less, or 3 hours or less. In one embodiment, either, neither, or both of the inoculation medium and the batch feed medium lack a reducing sugar.

In one embodiment, the continuous feed of a reducing sugar is by perfusion cell culture in which the reducing sugar is supplied in the cell culture medium during perfusion. In one embodiment, an inoculation medium and/or a batch feed medium are contacted with the host cells before perfusion cell culturing during expression of the polypeptide by the host cell. In one embodiment of the invention comprising perfusion cell culturing, the cells are maintained in a cell culture medium without further addition of reducing sugar for a period of time before the harvesting, wherein the period of time is 72 hours or less, 48 hours or less, 36 hours or less, 24 hours or less, 12 hours or less, 6 hours or less, or 3 hours or less. In one embodiment, either, neither, or both of the inoculation medium and the batch feed medium lack a reducing sugar.

In one embodiment, glycation of the polypeptide is 70% or less of the glycation of the polypeptide produced by a control method. In one embodiment, glycation alternatively is 60% or less, 40% or less, 20% or less, 10% or less, or 5% or less of the glycation of the polypeptide produced by a control method. The amount that the glycation is reduced by the method of the invention is determined by comparing the average glycation level of the polypeptide produced according to the invention to the average glycation level of the polypeptide produced by a control method comprising more than 5 g/L reducing sugar in the culture medium, comprising reducing sugar in the inoculation medium and/or in a batch feed, or a combination of these features.

Each of the references cited herein is hereby incorporated by reference in its entirety. Further objects, features, and advantages of the invention will become apparent from the detailed description that follows.

BRIEF DESCRIPTION OF THE DRAWINGS

FIG. 2a is a bar graph comparing antibody glycation at the time of harvest (Day 12) in six parallel cultures of clone 2 expressing the antibody. FIG. 2b is a graph of glucose concentration over time for the control method used in the 2 L bioreactor experiments.

FIG. 3a is graph of antibody glycation in reduced glucose fed batch experiments comparing antibody glycation in cultures of various clones expressing the antibody. FIG. 3b is a graph of glucose concentration over time for the reduced glucose fed batch culture method used in the 2 L bioreactor experiments.

FIG. 5a is a graph comparing antibody glycation in reduced glucose fed batch culture versus antibody glycation in semi continuous feed culture. FIG. 5b is a graph of glucose concentration over time for the reduced glucose fed batch and the semi continuous glucose feed cultures.

FIG. 6a is a graph comparing antibody glycation in reduced glucose fed batch culture versus antibody glycation in semi continuous glucose feed and fully continuous glucose feed cultures. FIG. 6b is a graph of glucose concentration over time for the reduced glucose fed batch, semi continuous glucose feed and fully continuous glucose feed cultures.

FIG. 7a is a graph comparing antibody glycation in reduced glucose fed batch culture versus antibody glycation in fully continuous glucose feed and continuous nutrient feed cultures. FIG. 7b is a graph of glucose concentration over time for the reduced glucose fed batch, fully continuous glucose feed, and continuous nutrient feed cultures.

DETAILED DESCRIPTION OF THE INVENTION

Definitions

Figure 1:
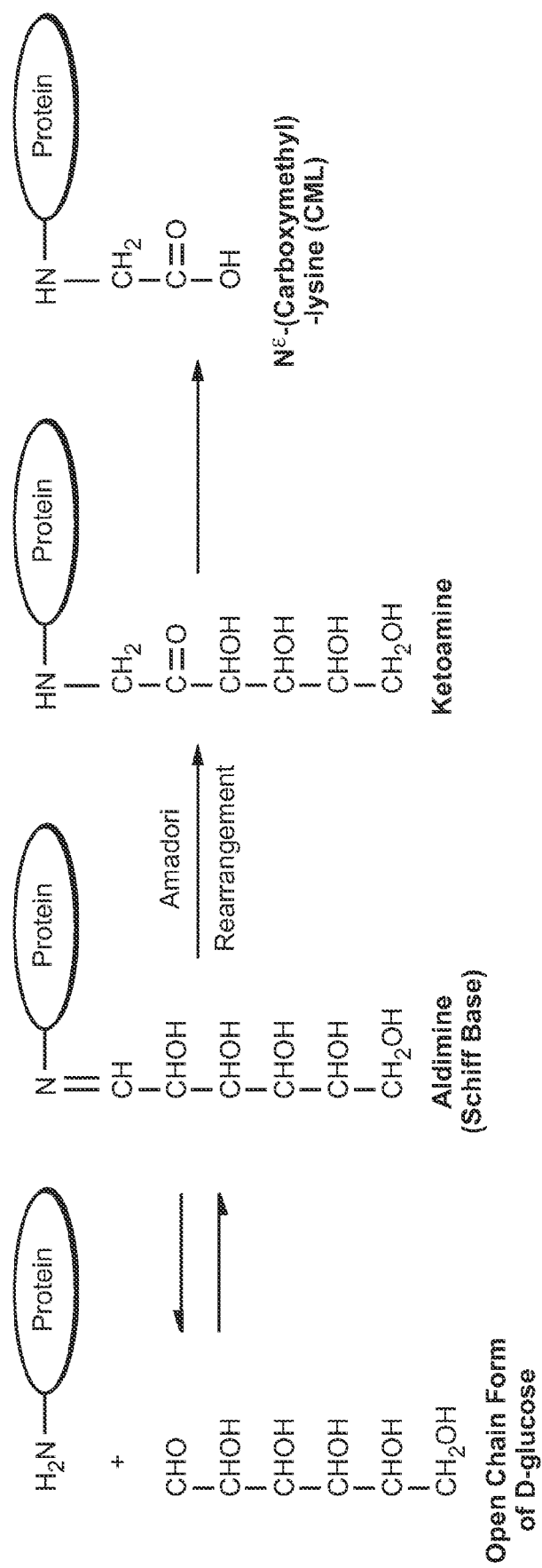
FIG. 1 depicts the reaction scheme for protein glycation and formation of $N^\epsilon$-(caarboxymethyl)-lysine (CML).

The process of the current invention can be used to produce polypeptides, including particular antibodies, in any type of host cells. The term "host cells" encompasses plant cells and animal cells. Animal cells encompass invertebrate, non-mammalian vertebrate (e.g., avian, reptile and amphibian) and mammalian cells. Examples of invertebrate cells include the following insect cells: *Spodoptera frugiperda* (caterpillar), *Aedes aegypti* (mosquito), *Aedes albopictus* (mosquito), *Drosophila melanogaster* (fruitfly), and *Bombyx mori* (See, e.g., Luckow et al., Bio/Technology, 6:47-55 (1988); Miller et al., in Genetic Engineering, Setlow, J. K. et al., eds., Vol. 8 (Plenum Publishing, 1986), pp. 277-279; and Maeda et al., Nature, 315:592-594 (1985)).

In one embodiment, the cells are mammalian cells. Examples of mammalian cells include human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59 (1977)); baby hamster kidney cells (BHK, ATCC CCL 10); Chinese hamster ovary cells/-DHFR (CHO, Urlaub and Chasin, Proc. Natl. Acad. Sci. USA, 77:4216 (1980)); mouse sertoli cells (TM4, Mather, Biol. Reprod., 23:243-251 (1980)); monkey kidney cells (CV1 ATCC CCL 70); African green monkey kidney cells (VERO-76, ATCC CRL-1587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 (1982)); MRC 5 cells; FS4 cells; and a human hepatoma line (Hep G2). In one embodiment, the cells are CHO cells.

The invention is also applicable to hybridoma cells. The term "hybridoma" refers to a hybrid cell line produced by the fusion of an immortal cell line of immunologic origin and an antibody producing cell. The term encompasses progeny of heterohybrid myeloma fusions, which are the result of a fusion with human cells and a murine myeloma cell line subsequently fused with a plasma cell, commonly known as a trioma cell line. Furthermore, the term is meant to include any immortalized hybrid cell line that produces antibodies such as, for example, quadromas (See, e.g., Milstein et al., Nature, 537:3053 (1983)). The hybrid cell lines can be of any species, including human and mouse.

In one embodiment, the mammalian cell is a non-hybridoma mammalian cell, which has been transformed with exogenous isolated nucleic acid encoding a polypeptide of interest, including, but not limited to, nucleic acids encoding antibodies, antibody fragments, such as ligand-binding fragments, and chimeric antibodies. By "exogenous nucleic acid" or "heterologous nucleic acid" is meant a nucleic acid sequence that is foreign to the cell, or homologous to the cell but in a position within the host cell nucleic acid in which the nucleic acid is ordinarily not found.

An isolated nucleic acid is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. An isolated nucleic acid is preferably a non-chromosomal nucleic acid, i.e. isolated from the chromosomal environment in which it naturally exists. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The term "reducing sugar" refers to sugars having an aldehyde or ketone group available, including without limitation glucose, galactose, fructose, ribose, and deoxyribose. A reducing sugar as used herein alternatively refers to a monosaccharide or a di- or polysaccharide in which a reducing sugar moiety is present at an end of the saccharide. A reducing sugar is typically capable of reacting with an amino acid side chain, such as the ε-amino acid group of a lysine or with arginine, resulting in glycation of the amino acid or a polypeptide comprising the amino acid.

The term "glucose" refers to either of alpha-D-glucose or beta-D-glucose, separately or in combination. It is noted that alpha- and beta-glucose forms are interconvertible in solution.

Figure 2A:
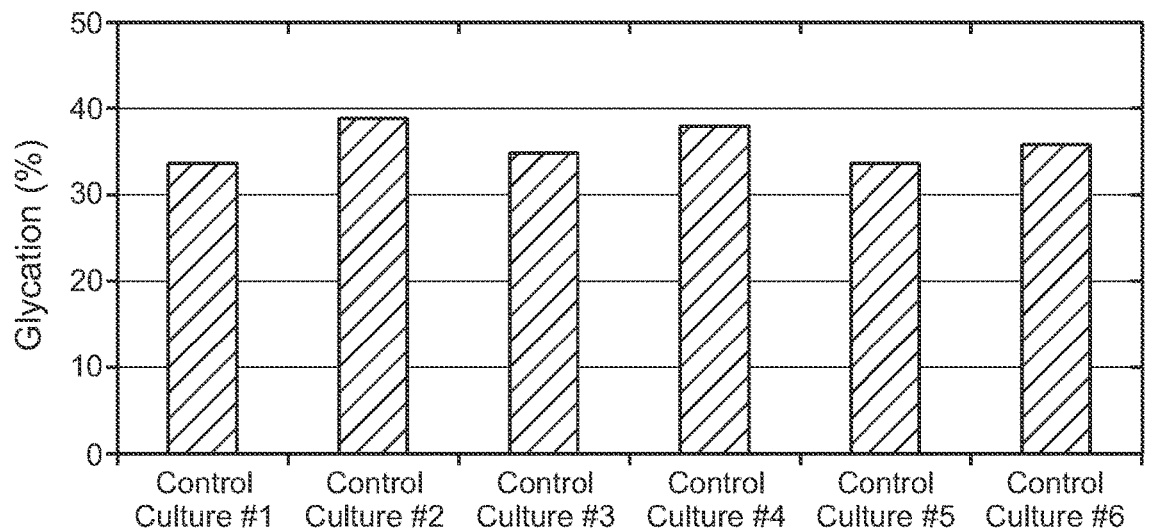
FIGS. 2a and 2b depict antibody glycation and glucose concentration in 2 L bioreactor experiments using the control cell culture method.
Figure 2B:
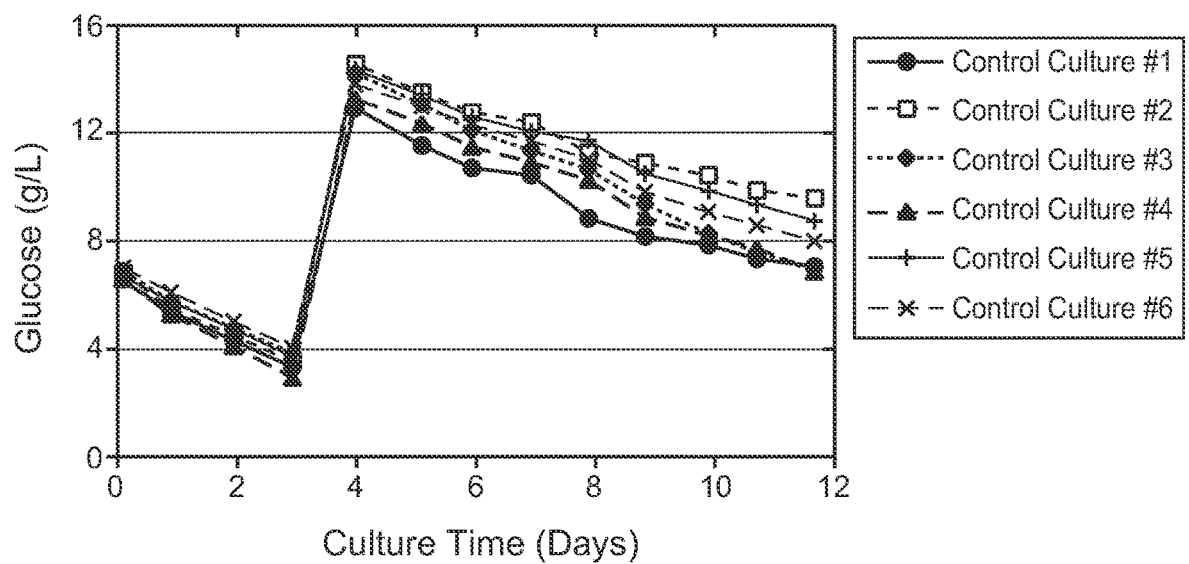

As used herein, the term "glycation" as applied to amino acids or polypeptides, or "glycation of the amino acid" or "glycation of the polypeptide" refers the nonenzymatic reaction of a reducing sugar, such as glucose, in the Maillard reaction as diagrammed in FIG. 1. The term "glycation" as applied to the amount of amino acids within a polypeptide that have undergone reaction with a reducing sugar, refers to the average level of glycation of the amino acids in the polypeptide available for glycation. One or more amino acids of the polypeptide may be available for glycation. Thus, the average level of glycation refers to the percentage of glycated amino acids in the polypeptide (calculated as: percent glycation=(glycated species)×100%/(glycated species+unglycated species)) detected in the glycated polypeptide (such as, for example, a polypeptide exposed to reducing sugar in a cell culture medium). The level of glycation is determined, for example, by chromatographic or spectroscopic methods capable of differentiating glycated from non-glycated polypeptides. For example, the extent of polypeptide glycation may be determined by boronate affinity chromatography as described herein. In brief, a 7.5×75 mm TSK Boronate 5PW column (Tosoh Bioscience, Inc., South San Francisco, Calif., USA) was used to separate the glycated antibodies from the unglycated forms (FIG. 2). Glycated antibodies were eluted from the column by using sorbitol to provide hydroxyl groups for competitive binding to the boronate ligand. Glycation may be expressed as the number of a particular amino acid in a polypeptide produced by a method of the invention relative to the number of that amino acid in the polypeptide glycated when the polypeptide is produced by a control method. Alternatively, glycation may be expressed as the average level of glycation of a polypeptide produced by a method of the invention relative to the average level of glycation of the polypeptide produced by a control method, wherein a relative reduction in glycation may be expressed. The latter determination may refer to glycation of a particular amino acid or it may refer to glycation of all amino acids that are glycated in the polypeptide.

The terms "amino acids" and "amino acid" refer to all naturally occurring alpha amino acids in both their D and L stereoisomeric forms, and their analogs and derivatives. An analog is defined as a substitution of an atom in the amino acid with a different atom that usually has similar properties. A derivative is defined as an amino acid that has another molecule or atom attached to it. Derivatives would include, for example, acetylation of an amino group, amination of a carboxyl group, or oxidation of the sulfur residues of two cysteine molecules to form cystine.

As used herein, "polypeptide" refers generally to peptides and proteins having more than about ten amino acids. The polypeptides may be homologous to the host cell, or preferably, may be exogenous, meaning that they are heterologous, i.e., foreign, to the host cell being utilized, such as a human protein produced by a Chinese hamster ovary cell, or a yeast polypeptide produced by a mammalian cell. Preferably, mammalian polypeptides (polypeptides that were originally derived from a mammalian organism) are used, more preferably those which are directly secreted into the medium.

Various polypeptides may be produced according to the invention. Examples of bacterial polypeptides include, e.g., alkaline phosphatase and beta-lactamase. Examples of mammalian polypeptides include molecules such as renin, a growth hormone, including human growth hormone; bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; mullerian-inhibiting substance; relaxin A-chain; relaxin B-chain; prorelaxin; mouse gonadotropin-associated peptide; a microbial protein, such as beta-lactamase; DNase; inhibin; activin; vascular endothelial growth factor (VEGF); receptors for hormones or growth factors; integrin; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-.beta.; platelet-derived growth factor (PDGF); fibroblast growth factor such as aFGF and bFGF; epidermal growth factor (EGF); transforming growth factor (TGF) such as TGF-alpha and TGF-beta, including TGF-.beta.1, TGF-.beta.2, TGF-.beta.3, TGF-.beta.4, or TGF-.beta.5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressing; regulatory proteins; antibodies; and fragments of any of the above-listed polypeptides.

Antibodies are other examples of mammalian polypeptides produced according to the invention. Antibodies are a preferred class of polypeptides that exhibit binding specificity to a specific antigen. Native antibodies are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. Exemplary antibodies are those that are directed against the antigens listed below.

"Antibody fragments" comprise a portion of an intact antibody, generally a portion comprising the antigen binding region or variable region of the intact antibody or the Fc region of an antibody which retains FcR binding capability. Examples of antibody fragments include linear antibodies; single-chain antibody molecules; and multispecific antibodies formed from antibody fragments. The antibody fragments preferably retain at least part of the hinge and optionally the CH1 region of an IgG heavy chain. More preferably, the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA* 81:6851-6855 (1984)).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity.

The term "hypervariable region", "HVR", or "HV", when used herein refers to the regions of an antibody variable domain which are hypervariable in sequence and/or form structurally defined loops. Generally, antibodies comprise six hypervariable regions: three hypervariable regions in the VH (H1, H2, H3); and three hypervariable regions in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures.

In some instances, Fv framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321: 522-525 (1986); Riechmann et al., Nature 332:323-329 (1988); and Presta, Curr. Op. Struct. Biol. 2:593-596 (1992).

An antibody is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) can also be used.

Where the antigen is a polypeptide, it may be a transmembrane molecule (e.g. receptor) or ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor VIIIC, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT-4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD3, CD4, CD8, CD18, CD19, CD20, and CD40; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the AIDS envelope; transport proteins; homing receptors; addressins; regulatory proteins; integrins such as CD11a, CD11b, CD11c, CD18, an ICAM, VLA-4 and VCAM; a tumor associated antigen such as HER2, HER3 or HER4 receptor; and fragments of any of the above-listed polypeptides.

Molecular targets for antibodies encompassed by the present invention include, but are not limited to, CD proteins such as CD3, CD4, CD8, CD18, CD19, CD22, CD20, CD34, and CD40; members of the ErbB receptor family e.g., the EGF receptor, HER2, HER3 or HER4 receptor; cell adhesion molecules e.g., LFA-1, Mac1, p150.95, VLA-4, ICAM-1, VCAM, MAdCAM (Briskin et al. (1993) Nature, 363:461-464; Shyjan et al. (1996) J. Immunol. 156:2851-2857), α4/β7 integrin (Kilshaw and Murant (1991) Eur. J. Immunol. 21:2591-2597; Gurish et al. (1992) 149: 1964-1972; and Shaw, S. K. and Brenner, M. B (1995) Semin. Immunol. 7:335), αE/β7 integrin, and αv/β3 integrin, and the subunits thereof, e.g., CD11a, CD11b, alpha4, alphaE (Cepek, K. L. et al. (1993) J. Immunol. 150:3459; Shaw, S. K. and Brenner, M. B. (1995) Semin. Immunol. 7:335), or β7 (Erle et al., (1991) J. Biol. Chem. 266:11009-11016); growth factors such as VEGF; tissue factor (TF); alpha interferon (α-IFN); interleukins, e.g., IL-8; IgE; blood group antigens; flk2/flt3 receptor; obesity (OB) receptor; mpl receptor; CTLA-4; protein C, and the like.

In one embodiment, the antibody is an antibody that binds to a human integrin subunit β7 and, more particularly, a humanized antibody that binds to a human integrin subunit β7 as disclosed in WO2006/026759, published Mar. 9, 2006, incorporated by reference in its entirety. In one embodiment, the humanized anti-β7 antibody is hu504.5, hu504.16, hu504.32, hu504.32M, hu504.32Q, or hu504.32R as disclosed in WO2006/026759, published Mar. 9, 2006. For example, in one embodiment the humanized anti-β7 antibody comprises one, two, three, four, five or six hypervariable regions (HVRs), wherein each HVR comprises, or consists essentially of, a sequence selected from the group consisting of SEQ ID NOs:1, 2, 3, 4, 5, 6, 7, 8, 9, 10, 11, 12, 13, 14, 15, 16, wherein SEQ ID NO:1, SEQ ID NO:7, SEQ ID NO:8 or SEQ ID NO:9 corresponds to an HVR-L1, SEQ ID NO:2 corresponds to an HVR-L2, SEQ ID NO:3 corresponds to an HVR-L3, SEQ ID NO:4 corresponds to an HVR-H1, SEQ ID NO:5 corresponds to an HVR-H2, and SEQ ID NOs:6 corresponds to an HVR-H3.

In another embodiment, the humanized anti-β7 antibody comprises HVR-L1, HVR-L2, HVR-L3, HVR-H1, HVR-H2, and HVR-H3, wherein HVR-L1 comprises SEQ ID NO:1, HVR-L2 comprises SEQ ID NO:2, HVR-L3 comprises SEQ ID NO:3, HVR-H1 comprises SEQ ID NO:4, HVR-H2 comprises SEQ ID NO:5, and HVR-H3 comprises SEQ ID NO:6.

In another embodiment, the humanized anti-β7 antibody comprises HVR-L1, HVR-L2, HVR-L3, HVR-H1, HVR-H2, and HVR-H3, wherein
HVR-L1 comprises SEQ ID NO:7 or SEQ ID NO:8.
HVR-L2 comprises SEQ ID NO:2,
HVR-L3 comprises SEQ ID NO:3,
HVR-H1 comprises SEQ ID NO:4,
HVR-H2 comprises SEQ ID NO:5, and
HVR-H3 comprises SEQ ID NO:6.

In another embodiment, the humanized anti-β7 antibody comprises HVR-L1, HVR-L2, HVR-L3, HVR-H1, HVR-H2, and HVR-H3, wherein HVR-L1 comprises SEQ ID NO:9,
HVR-L2 comprises SEQ ID NO:2,
HVR-L3 comprises SEQ ID NO:3,
HVR-H1 comprises SEQ ID NO:4,
HVR-H2 comprises SEQ ID NO:5, and
HVR-H3 comprises SEQ ID NO:6, SEQ ID NO:10, SEQ ID NO:11, SEQ ID NO:12, or SEQ ID NO:13.

In another embodiment, the humanized anti-β7 antibody comprises HVR-L1, HVR-L2, HVR-L3, HVR-H1, HVR-H2, and HVR-H3, wherein
HVR-L1 comprises SEQ ID NO:9,
HVR-L2 comprises SEQ ID NO:14 or SEQ ID NO:15,
HVR-L3 comprises SEQ ID NO:3,
HVR-H1 comprises SEQ ID NO:4,
HVR-H2 comprises SEQ ID NO:5, and
HVR-H3 comprises SEQ ID NO:11.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein. Examples of BsAbs include those with one arm directed against a tumor cell antigen and the other arm directed against a cytotoxic trigger molecule such as anti-FcγRI/anti-CD15, anti-p185$^{HER2}$/FcγRIII (CD16), anti-CD3/anti-malignant B-cell (1D10), anti-CD3/anti-p185$^{HER2}$, anti-CD3/anti-p97, anti-CD3/anti-renal cell carcinoma, anti-CD3/anti-OVCAR-3, anti-CD3/L-D1 (anti-colon carcinoma), anti-CD3/anti-melanocyte stimulating hormone analog, anti-EGF receptor/anti-CD3, anti-CD3/anti-CAMA1, anti-CD3/anti-CD19, anti-CD3/MoV18, anti-neural cell ahesion molecule (NCAM)/anti-CD3, anti-folate binding protein (FBP)/anti-CD3, anti-pan carcinoma associated antigen (AMOC-31)/anti-CD3; BsAbs with one arm which binds specifically to a tumor antigen and one arm which binds to a toxin such as anti-saporin/anti-Id-1, anti-CD22/anti-saporin, anti-CD7/anti-saporin, anti-CD38/anti-saporin, anti-CEA/anti-ricin A chain, anti-interferon-α (IFN-α)/anti-hybridoma idiotype, anti-CEA/anti-vinca alkaloid; BsAbs for converting enzyme activated prodrugs such as anti-CD30/anti-alkaline phosphatase (which catalyzes conversion of mitomycin phosphate prodrug to mitomycin alcohol); BsAbs which can be used as fibrinolytic agents such as anti-fibrin/anti-tissue plasminogen activator (tPA), anti-fibrin/anti-urokinase-type plasminogen activator (uPA); BsAbs for targeting immune complexes to cell surface receptors such as anti-low density lipoprotein (LDL)/anti-Fc receptor (e.g. FcγRI, FcγRII, FcγRIIB, or FcγRIII); BsAbs for use in therapy of infectious diseases such as anti-CD3/anti-herpes simplex virus (HSV), anti-T-cell receptor:CD3 complex/anti-influenza, anti-FcγR/anti-HIV; BsAbs for tumor detection in vitro or in vivo such as anti-CEA/anti-EOTUBE, anti-CEA/anti-DPTA, anti-p185$^{HER2}$/anti-hapten; BsAbs as vaccine adjuvants; and BsAbs as diagnostic tools such as anti-rabbit IgG/anti-ferritin, anti-horse radish peroxidase (HRP)/anti-hormone, anti-somatostatin/anti-substance P, anti-HRP/anti-FITC, anti-CEA/anti-β-galactosidase. Examples of trispecific antibodies include anti-CD3/anti-CD4/anti-CD37, anti-CD3/anti-CD5/anti-CD37 and anti-CD3/anti-CD8/anti-CD37. Bispecific antibodies can be prepared as full length antibodies or antibody fragments (e.g. F(ab')$_2$ bispecific antibodies).

Methods for making bispecific antibodies are known in the art. Traditional production of full-length bispecific antibodies is based on the coexpression of two immunoglobulin heavy chain-light chain pairs, where the two chains have different specificities (Millstein et al., *Nature,* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation (see WO 94/04690). For further details of generating bispecific antibodies see, for example, Suresh et al., *Methods in Enzymology,* 121:210 (1986). According to another approach, the interface between a pair of antibody molecules can be engineered to maximize the percentage of heterodimers which are recovered from recombinant cell culture (see WO96/27011). The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (see U.S. Pat. No. 4,676,980), and for treatment of HIV infection (see WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies are contemplated. For example, trispecific antibodies can be prepared (see Tutt et al. *J. Immunol.* 147: 60 (1991)).

Preferred antibodies produced by the method of the invention include without limitation anti-HER2, antibody 2C4, anti-VEGF, antibody C2B8, antiCD11a, anti-tissue factor, IgG4b, anti-CD40, anti-CD20, anti-IgE, E25, and E26.

The terms "cell culture medium" and "culture medium" refer to a nutrient solution used for growing host cells that typically provides at least one component from one or more of the following categories:

1) an energy source, usually in the form of a carbohydrate such as a reducing sugar, such as glucose;
2) all essential amino acids, and preferably, and most commonly, the basic set of twenty amino acids plus cysteine;
3) vitamins and/or other organic compounds required at low concentrations;
4) free fatty acids; and
5) trace elements, where trace elements are defined as inorganic compounds or naturally occurring elements that are typically required at very low concentrations, usually in the micromolar range.

The nutrient solution may optionally be supplemented with one or more components from any of the following categories:

1) hormones and other growth factors as, for example, insulin, transferrin, and epidermal growth factor;
2) salts and buffers as, for example, calcium, magnesium, and phosphate;
3) nucleosides and bases such as, for example, adenosine and thymidine, hypoxanthine; and
4) protein and tissue hydrolysates.

The growth phase refers to the period of exponential growth where cells are generally rapidly dividing, e.g., "growing". During this phase, cells are cultured for a period of time, usually 1 to 4 days, e.g. 1, 2, 3, or 4 days, and under such conditions that cell growth is optimal. The determination of the growth cycle for the host cell can be determined for the particular host cell by methods known to those skilled in the art.

As used herein, the term "continuous feed" or "continuous feeding" in a cell culture process refers to the semi continuous or fully continuous addition of compound, such as a cell culture medium nutrient, into the cell culture. Typically, and as used herein, a continuous feed is performed during the production phase. The continuous addition of cell culture nutrient may be performed using a peristaltic pump, or any automatic or manual device or manually such that the nutrient is added continuously, or in such increments, that the level of nutrient in the cell culture is maintained at a predetermined concentration with typical deviation for cell culture and fermentation polypeptide production. Such typical deviation may be alternatively +/−10% or less, +/−5% or less, or +/−2% or less. According to one embodiment of the present invention, continuous feed is performed during the production phase to maintain the concentration of reducing sugar, such as glucose, at 5 g/L with a deviation of +/−25% or less, +/−20% or less, +/−10% or less, +/−5% or less, or +/−2% or less in the cell culture medium. In one embodiment, the continuous feed used is a glucose solution and is referred to herein as a "glucose feed." In another embodiment, the continuous feed used is a concentrated nutrient mixture of production medium components including glucose and is referred to herein as a "nutrient feed" or "nutrient supplement."

As used herein, the term "inoculum" refers to a volume of host cells harvested from growing in a culture medium for addition to a culture medium at the beginning of a production phase. Preferably, the animal cells are "expanded" during the growing, whereby as the cells divide and increase in cell number (i.e., cell density), the cells are transferred to a larger volume of growth medium for continued growth. Preferably, the inoculum has a cell density of from about 0.5% packed cell volume (PCV) to and including about 2.5% PCV, more preferably from about 1% PCV to and including about 2% PCV. Preferably the inoculum volume is one-fifth the volume of the culture medium to be used in the production phase. According to the invention, the host cells are preferably mammalian cells, more preferably CHO cells.

As used herein, the term "seeding" refers to the addition or inoculation of growing cells into a culture medium at the beginning of the production phase. The production phase is typically the phase in which host cells express the polypeptide of interest. Further, as used herein, the term "seed train" refers to a continual passaging of cells in volumes of culture medium of about 20 L or less for the maintenance of the cell line.

As used herein, the phrases, "batch feed" or "fed batch cell culture," refer to a batch culture wherein the host cells and culture medium are supplied to the culturing vessel initially, and additional culture nutrients are fed, in discrete increments, to the culture during the culturing process. Fed batch culture is distinguished from simple "batch culture" in which all components for cell culturing (including the animal cells and all culture nutrients) are supplied to the culturing vessel at the start of the culturing process. Fed batch culture can be further distinguished from perfusion culturing insofar as the supernate is not removed from the culturing vessel during the process. Batch feed typically comprises nutrients useful for growth of the host cell. In the present examples disclosed herein batch feed for control methods comprised nutrients (salts, vitamins, and the like) plus reducing sugar. Subsequent additions (feeds) of reducing sugar are typically provided in discrete additions in methods other than those of the present invention. In continuous reducing sugar feed methods of the invention, reducing sugar feeds subsequent to batch feed (lacking reducing sugar) are performed by continuous feed as disclosed herein.

As used herein, "perfusion culturing," "perfusion cell culturing," or "perfusion culture" refers to a cell culturing method in which the cultured cells are restrained in the culture by, e.g., filtration, encapsulation, anchoring to microcarriers, etc., and the culture medium is continuously or intermittently introduced and removed from the culturing vessel. However, removal of samples for testing purposes during fed batch cell culture is contemplated. According to one embodiment of the invention, continuous feeding of the reducing sugar is performed by a perfusion culturing process in which perfusion culture medium containing glucose is added semi continuously or fully continuously in a standard perfusion cell culture process such that the concentration of glucose is about 5 g/L or less, 4 g/L or less, 3 g/L or less, 2 g/L or less, or 1 g/L or less during the majority of the production phase.

As used herein, the term "control culture method" or "control cell culture method" refers to a method other than a method of the invention. As non-limiting examples, a control cell culture method does not comprise a continuous feed process during the production phase when host cells express a polypeptide of interest. Alternatively, a control cell culture method comprises a continuous feed process that maintains reducing sugar concentration at greater than 5 g/L.

Methods of Carrying Out the Invention

The present invention provides benefits of improved cell culture of desired polypeptides, such as an antibody expressed from a heterologous nucleic acid within a cell in the culture, through manipulation of discrete factors during the culturing processes based on a greater understanding of the principal effects of and interactions between the various process parameters. In particular, as disclosed herein, manipulation processes for providing a reducing sugar, such as glucose, during the cell culture production phase such that glycation of the desired polypeptide is reduced relative to the polypeptide produced by a control cell culture method. The method of the present invention provides a continuous feed of a reducing sugar or a nutrient supplement containing reducing sugar such that the reducing sugar is present in the cell culture at a concentration of 5 g/L or less during the majority of the production phase.

Cell Culture Procedures

Mammalian cell culture procedures useful for practicing the invention are described herein.

1. Cell Culture Growth Phase

An initial step of the process of the invention is a growth phase, wherein batch cell culture conditions provide for growth of recombinant animal cells, to produce a seed train. The growth phase refers to the period of exponential growth where cells are generally rapidly dividing, e.g. growing. During this phase, cells are cultured for a period of time, usually 1 to 4 days, e.g. 1, 2, 3, or 4 days, and under such conditions that cell growth is optimal. The determination of the growth cycle for the host cell can be determined for the particular host cell by methods known to those skilled in the art.

In the growth phase, the basal culture medium and host cells are supplied to the culturing vessel in batch. The culture medium is preferably free of serum, e.g. less than about 5%, preferably less than 1%, more preferably 0 to 0.1% serum, and other animal-derived proteins. However, they can be used if desired. The cell culture medium typically comprises amino acids, vitamins, trace elements and other media components as generally known to those skilled in the art.

Alternatively, commercially available media such as Ham's F10 (Sigma), Minimal Essential Medium ([MEM], Sigma), RPMI-1640 (Sigma), and Dulbecco's Modified Eagle's Medium ([DMEM], Sigma) are suitable for culturing animal cells. In addition, any of the media described in Ham and Wallace, Meth. Enz., 58:44 (1979), Barnes and Sato, Anal. Biochem., 102:255 (1980), U.S. Pat. Nos. 4,767,704; 4,657,866; 4,927,762; or 4,560,655; WO 90/03430; WO 87/00195; U.S. Pat. No. Re. 30,985; or U.S. Pat. No. 5,122,469, the disclosures of all of which are incorporated herein by reference in their entirety, may be used as culture media for the host cells.

Any of these media may be supplemented as necessary with hormones and/or other growth factors (such as insulin, transferrin, or epidermal growth factor), ions (such as sodium, chloride, calcium, magnesium, and phosphate), buffers (such as HEPES), nucleosides (such as adenosine and thymidine), trace elements (defined as inorganic compounds usually present at final concentrations in the micromolar range), and glucose or an equivalent energy source. Any other necessary supplements may also be included at appropriate concentrations that would be known to those skilled in the art.

The initial cell culture medium may comprise a reducing sugar at a concentration in the initial growth phase (the inoculum) of less than 8 g/L. For fed batch cultures, the concentration of reducing sugar in the batch feed range from approximately 20 g/L to approximately 60 g/L.

At a particular point in their growth, the cells may form an inoculum to inoculate a culture medium at the start of culturing prior to the production phase. Alternatively, the production phase may be continuous with the growth phase.

A suitable initial cell seed density for the cell growth phase is in the range $3 \times 10^5$ to $1.5 \times 10^6$ cells/ml, for example. A suitable culturing vessel for cell growth is a pH controlled bioreactor. An autoclavable glass fermenter (sold by Applikon, Foster City, Calif.) or stainless steel fermenter (sold by Biolafitte, Princeton, N.J.) can be used. Other culturing vessels suitable for practicing the invention are well known in the art.

While the cells of the growth phase need not be transformed with exogenous nucleic acid, in the preferred embodiment of the invention, the cell growth phase is followed by a distinct polypeptide, e.g., antibody production phase wherein the cells have been transformed with exogenous nucleic acid encoding the polypeptide of interest. Suitable methods for transformation of the animal cells follow.

2. Transformation of Host Cells

Methods, vectors, and host cells suitable for adaptation to the synthesis of the polypeptide of interest in recombinant vertebrate cell culture are described in Gething et al., Nature, 293:620-625 (1981); Mantei et al., Nature, 281:40-46 (1979); Levinson et al.; EP 117,060; and EP 117,058. A particularly useful plasmid for mammalian cell culture expression of the polypeptide is pRK5 (EP pub. no. 307,247) or pSVI6B (PCT pub. no. WO 91/08291 published Jun. 13, 1991).

Host cells are transformed with expression or cloning vectors and cultured in nutrient media modified as appropriate for inducing promoters, selecting transformants, or amplifying the genes encoding the desired sequences. For mammalian cells, the calcium phosphate precipitation method of Graham and van der Erb, Virology, 52:456-457 (1978) or the Lipofectamine™ (Gibco BRL) Method of Hawley-Nelson, Focus 15:73 (1193) are preferred. General aspects of mammalian cell host system transformations have been described by Axel in U.S. Pat. No. 4,399,216 issued Aug. 16, 1983. For various techniques for transforming mammalian cells, see Keown et al., Methods in Enzymology (1989), Keown et al., Methods in Enzymology, 185:527-537 (1990), and Mansour et al., Nature, 336:348-352 (1988).

The invention also encompasses hybridomas which secrete monoclonal antibodies in cell culture. Monoclonal antibodies are prepared by recovering immune cells (typically spleen cells or lymphocytes from lymph node tissue) from immunized animals and immortalizing the cells in conventional fashion, e.g., by fusion with myeloma cells or by Epstein-Barr (EB)-virus transformation and screening for clones expressing the desired antibody. The hybridoma technique described originally by Kohler and Milstein, Eur. J. Immunol., 6:511 (1976), and also described by Hammerling et al., In: Monoclonal Antibodies and T-Cell Hybridomas, Elsevier, N.Y., pp. 563-681 (1981) has been widely applied to produce hybrid cell lines that secrete high levels of monoclonal antibodies against many specific antigens.

3. Polypeptide Production Phase of the Cell Culture

The cell growth phase is generally followed by a polypeptide production phase, which is distinct therefrom. During culturing, the cells are manipulated in a production phase so that they express the desired polypeptide. This phase generally begins at least 3 hours after the beginning of the growth phase, such as at about 12 to about 224 hours, or alternatively at about 120 to 192 hours after the beginning of the growth phase. The production phase can last, e.g., from 4 to 14 days. Alternatively, the production phase may be 18-21 days or longer. During this phase, cell growth has generally plateaued, e.g., logarithmic cell growth has ended and protein production is primary. During this period, as discussed below, the medium is supplemented with glucose and optionally other components. According to the invention, the cell culture is supplemented with glucose (or other reducing sugar or mixture of reducing sugars) either by a continuous glucose feed or a continuous nutrient supplement feed (containing glucose) such that the concentration of reducing sugar is less than 5 g/L during the majority of the production phase. The production phase may be carried out in a different culturing vessel from the cell growth phase. However, the same vessel can be employed for each step.

The production phase involves inoculating the cultured host cells of the growth phase at a cell seed density of generally at least about $0.5 \times 10^6$ cells/mL, preferably in the range $1.0$-$3.0 \times 10^6$ cells/mL. The same media as used in the initial growth steps can be used. However, batch additions of glucose and optionally other components are made.

In order to achieve a culture medium having the desired reducing sugar (such as glucose) concentration, a cell culture medium providing the reducing sugar can be used. According to the invention, the reducing sugar is maintained in the cell culture at less than 5 g/L during the majority of the production phase using a continuous feed process. Also, the culture medium preferably contains a amino acids, vitamins, salts and other components (other than a reducing sugar) in order to provide additional cell nutrients.

The production phase is preferably carried out in the presence of a concentration of glucose controlled throughout the culturing to be within a range between about 0.5 g/L to about 5 g/L. This amount can be added continuously, semi continuously, or in multiple increments such that the glucose (or other reducing sugar(s)) concentration in the culture medium during the majority of the production phase is essentially constant (such as +/-10% or less, +/-5% or less, or +/-2% or less deviation from a predetermined concentration).

Intermittent off-line sampling of the culture medium can be carried out. The reducing sugar concentration of the culture medium can then be modified, manually or automatically, by the modulation of a reducing sugar feed solution as required.

Temperature in the growth phase and optional inoculum growth phase is generally maintained within a range of 35° C. and 39° C., and preferably is maintained at 37° C. The initial temperature of the production culture should also preferably be maintained at the same temperature as the prior phase, e.g., 37° C. After a certain period of production, the temperature is preferably shifted down. It is advantageous to use a temperature shift to lower the temperature, since at lower temperatures glucose and lactate metabolism are reduced, and therefore culture viability can be enhanced by delaying the onset of apoptosis. Where a temperature shift is including in the culturing method, the temperature is preferably shifted down from about 37-39° C. by about 2 to about 8 degrees C., more preferably about 3, 4, 5, or about 6 degrees C. such that the final temperature during the production phase is from about 37° C. to and including about 29° C. The temperature shift can occur at any point after the start of the production phase, and can occur as early as 3 hours after the start of the culturing step and as late as 96 hours, and can occur between about 12 and 72 hours after the start of production. The temperature shift can occur, for example, at about 3 hours, up to about 12 hours, up to about 24 hours, up to about 36 hours, up to about 48 hours, up to about 56 hours, up to about 72 hours, or up to about 96 hours after the start of the production phase.

To maintain cell viability and productivity, additional quantities of some production medium components, in the form of a concentrated nutrient mixture, termed a "batch feed," can be fed to the production vessel at specified times during culturing. A batch feed is preferably the source of additional glucose during the production phase. Batch feed should be added at a time after which additions of glucose will have positive effects, and generally at least 12 hours after initiation of the culturing phase. For example, batch feed is preferably added between 12 and 120 hours after the start of culturing, such as after inoculation of cell culture. Batch feed additions may be effected through addition of concentrated batch feed in the form used in the initial culturing, or modified to remove components. In addition, batch feed may be added which contains no reducing sugar (such as no glucose), or which has a reduced reducing sugar content. In the continuous nutrient feed method of the invention, the batch feed containing reducing sugar (such as glucose) is termed "nutrient feed" and is added continuously to the cell culture starting at, for example, 72 hours, and is added at a rate such as to maintain the reducing sugar concentration within a target range, such as 3 to 5 g/L. Alternatively, the batch feed is added once in the cell culturing process at, for example, 72 hours, and is a concentrated solution of nutrients having a different composition than the culture medium, plus glucose at a concentration of from about 20 g/L to about 60 g/L. In methods other than the continuous reducing sugar (such as glucose) feed method and the continuous nutrient feed of the invention, subsequent discrete feeds of reducing sugar may be performed when the reducing sugar concentration drops to a chosen level. Typically, additional nutrients (other than reducing sugar) are not added in the feeds subsequent to the batch feed.

4. Polypeptide Purification

The polypeptide of interest preferably is recovered from the culture medium as a secreted polypeptide, although it also may be recovered from host cell lysates when directly expressed without a secretory signal. A preferred polypeptide produced by the method of the invention is an antibody, more preferably a monoclonal antibody.

As a first step, the culture medium or lysate is centrifuged to remove particulate cell debris. The polypeptide thereafter is purified from contaminant soluble proteins and polypeptides, with the following procedures being exemplary of suitable purification procedures: by fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; gel filtration using, for example, Sephadex G-75; and protein A Sepharose columns to remove contaminants such as IgG. A protease inhibitor such as phenyl methyl sulfonyl fluoride (PMSF) also may be useful to inhibit proteolytic degradation during purification. One skilled in the art will appreciate that purification methods suitable for the polypeptide of interest may require modification to account for changes in the character of the polypeptide upon expression in recombinant cell culture. In a preferred example, antibodies can be generally purified using chromatographic techniques (e.g., protein A, affinity chromatography with a low pH elution step and ion exchange chromatography to remove process impurities).

EXAMPLES

The following examples of the practice of the invention are presented by way of illustration and not by way of limitation.

Example 1

Cell Culture for Reduction of Antibody Glycation

During production, a humanized anti-beta7 monoclonal antibody (see WO2006/026759) was found to be approximately 40-60% glycated compared to approximately 5% glycation for other recombinant antibodies that were also analyzed. The predominant glycation site was identified as lysine 49 on the light chain by utilizing multiple techniques, including N-terminal sequence analysis, MALDI-TOF MS, and ESI-MS tandem mass spectrometry (Zhang, B. et al., WCBP 2006: 10$^{th}$ Symposium on the interface of regulatory and analytical sciences for biotechnology health products. Jan. 24-27, 2006, San Francisco, Calif., USA). An in vitro study of IgG glycation at physiological glucose concentration showed that IgG was glycated at both light and heavy chains, and the data suggested that glycation sites were equally distributed throughout the IgG molecule (Vrdoljak, A., Clinica Chimica Acta 345:105-111 (2004)).

Cell Culture

Recombinant Chinese Hamster Ovary (CHO) cells derived from dihydrofolate reductase minus (dhfr⁻) DUKX CHO host, were used in all examples (See Urlaub G., Chasin L. A. *Isolation of Chinese Hamster Cell Mutants Deficient in Dihydrofolate Reductase Activity*, Proc. Natl. Acad. Sci. USA, 77: 41216-4220). CHO cells were genetically engineered to secrete recombinant humanized anti-integrin beta7 monoclonal antibody using a dhfr/methoxrexate selection method similar to that used by Kaufman and Sharpe (See Kaufman R. J., Sharpe P. A. *Amplification and Expression of Sequences Cotransfected with a Modular Dihydrofolate Reductase Complementary DNA Gene*. J. Mol. Biol. 1982, 159, 601-621). Cells were cultured in serum-free medium. The same production cell culture medium was used for the plate cultures, spinner flask cultures and bioreactor cultures. Glucose was the source of reducing sugar available in the culture medium.

Analytical Methods

Recombinant humanized antibody titers were quantified by Protein A affinity chromatography. Glucose concentrations in culture media were measured by Nova BioProfile™ 400 Analyzer (Nova Biomedical, Waltham, Mass., USA). The extent of product glycation was determined by boronate affinity chromatography using 7.5×75 mm TSK™ Boronate 5PW column (Tosoh Bioscience, Inc., South San Francisco, Calif., USA) to separate the glycated antibodies from the unglycated forms (see FIG. 2). The mobile phases were A: 50 mM N-[2-hydroxyethyl]piperazine-N'-[3-propanesulfonic acid] (EPPS), 20 mM Tris, 200 mM NaCl, pH 8.7, and B: 500 mM sorbitol in buffer A. The glycated form of the antibody was retained while the unglycated form was unretained. Glycated antibodies were eluted from the column by adding sorbitol to the elution buffer to provide hydroxyl groups for competitive binding to the boronate ligand, thereby eluting the glycated antibodies.

Bioreactor Experiments to Reduce Antibody Glycation

Cells were cultured in stirred tank bioreactors (Applikon, Foster City, Calif.). Three days post-inoculation, batch feed was added to each bioreactor at a feed volume of 250 mL for every liter of cell culture. The batch feed glucose concentration was approximately 60 g/L in the 40 L bioreactor experiments as well as in the 2 L bioreactor experiments testing the control method and the continuous nutrient feed method. In all the other 2 L bioreactor experiments, the glucose concentration in the batch feed was either approximately 20-30 g/L or it lacked glucose, as specified. The pH, dissolved oxygen, and temperature profiles were controlled identically in all the bioreactors.

Continuous Glucose Feed Setup

In preparation for continuous glucose feed operation, a low-speed peristaltic pump (Watson-Marlow 101U/R) was calibrated to determine the pump flow rates at each pump speed setting for the pump tubing used in the experiment. To set up a bioreactor for continuous glucose feed operation, a bottle of concentrated glucose solution (167 mg/L) was connected to a bioreactor feed port via pump tubing. To initiate continuous glucose feed, a peristaltic pump operating continuously was used to transfer the glucose solution from the bottle into the bioreactor. During the continuous glucose feed process, the pump rate was adjusted daily based on the projected glucose uptake by the culture for the next day.

Continuous Nutrient Feed Setup

In preparation for continuous nutrient feed operation, a low-speed peristaltic pump (Watson-Marlow 101U/R) was calibrated to determine the pump flow rates at each pump speed setting for the pump tubing used in the experiment. To set up a bioreactor for continuous nutrient feed operation, a bottle of batch feed (nutrient mixture including approximately 60 g/L glucose) was connected to a bioreactor feed port via pump tubing. To initiate continuous nutrient feed, a peristaltic pump operating continuously was used to transfer the batch feed from the bottle into the bioreactor. During the continuous nutrient feed process, the pump rate was adjusted daily based on the projected glucose uptake by the culture for the next day.

Example 2

Glycation of Antibody is Extracellular and Not Clone Specific

Several clones of the humanized anti-beta7 transfected CHO cell lines were tested to determine whether variation in the level of glycation may be attributed to clone-to-clone variation.

Clones were inoculated on 60 mm plates containing in production medium. No batch feed or glucose was added to the plates during culturing. Maximum glucose level in the plates was at Day 0 (about 7 g/L glucose). The plates were inoculated at 37° C. and then at Day 1, the temperature was shifted to 33° C. Cells were allowed to grow at 33° C. for 13 days, for a total production time of 14 days from seeding to harvest. Antibody was secreted into the culture medium.

Antibody was isolated from the culture media in all experiments performed herein by passing the post-production cell culture medium through a Protein A affinity chromatography column followed by elution of the antibody. The antibody was subsequently analyzed for glycation level.

The percent glycation of antibody isolated from each clone was determined using the chromatographic method described in Example 1 herein.

Antibody expression by the different CHO clones in 60 mm plates demonstrated no significant differences in glycation (see Table 1). This result indicates that glycation of the expressed antibody is an extracellular event and is not clone-specific.

TABLE 1

Glycation of antibody produced by different CHO clones in 60 mm plates.

| Clone | 2 | 25 | 92 | 131 | 169 | 191 | 260 | 274 | 277 |
|---|---|---|---|---|---|---|---|---|---|
| Glycation (%) | 19 | 21 | 20 | 18 | 19 | 17 | 18 | 18 | 20 |

Example 3

Glycation Level is Affected by Cultivation Time and Glucose Concentration

Glycation of antibody produced in 40 L bioreactors and 1 L spinner flasks was compared. In the spinner flasks, the initial glucose concentration was about 7 g/L and the final glucose concentration was less than 6 g/L. The inoculum for the spinner flasks was the same as for the bioreactors, but there was no batch feed and no additions of glucose. The cells were cultured in the spinner flasks at 37° C. with a temperature shift to 33° C. at Day 1. In the 40 L bioreactor experiments, the initial glucose concentration (at Day 0) was about 7 g/L and, after the batch feed (nutrients plus approximately 60 g/L glucose) was performed at Day 3 or 4, the glucose concentration was increased to about 13-14 g/L. After the batch feed, the glucose concentration decreased to about 7-11 g/L at harvest. Antibody was harvested and glycation was determined according to the method described in Example 1 herein.

Antibody glycation was approximately 40%-60% in 40 L bioreactors and approximately 10%-15% in 1 L spinner flasks at the time of harvest (see Table 2). The higher glycation levels in antibody produced in 40 L bioreactors is attributed to the longer cultivation time and the higher concentration of glucose in the culture medium.

TABLE 2

Glycation of antibody produced in 40 L bioreactors and 1 L spinners.

| Vessel | Volume | Harvest Clone | Time | Final [Glucose] | Glycation |
|---|---|---|---|---|---|
| Bioreactor | 2 × 40 L | 2 | Day 11 and Day 14 | >9 g/L | 42% |
| Bioreactor | 40 L | 2 | Day 14 | >10 g/L | 58% |
| Bioreactor | 40 L | 2 | Day 14 | >7 g/L | 42% |
| Spinner | 1 L | 2 | Day 5 | <6 g/L | 13% |
| Spinner | 1 L | 191 | Day 5 | <6 g/L | 11% |

Example 4

Glycation Level Using Control Cell Culture Method

Clone 2 was cultured in six parallel 2 L experiments using an in-house generic bioreactor process referred to herein as the "control cell culture method" or the "control culture method." In this set of 2 L control experiments, the initial glucose concentration was approximately 7 g/L. The batch feed (nutrients plus approximately 60 g/L glucose) was added to the bioreactors after Day 3, and the glucose concentrations in all the cultures increased to approximately 12-14 g/L as measured on Day 4. At the time of harvest (Day 12), the glucose concentrations were approximately 7-10 g/L, and the antibody glycation was approximately 34-40% (see FIG. 2).

Example 5

Glycation is Lowered Using Reduced Glucose Fed Batch Cell Culture Method

Figure 3A:
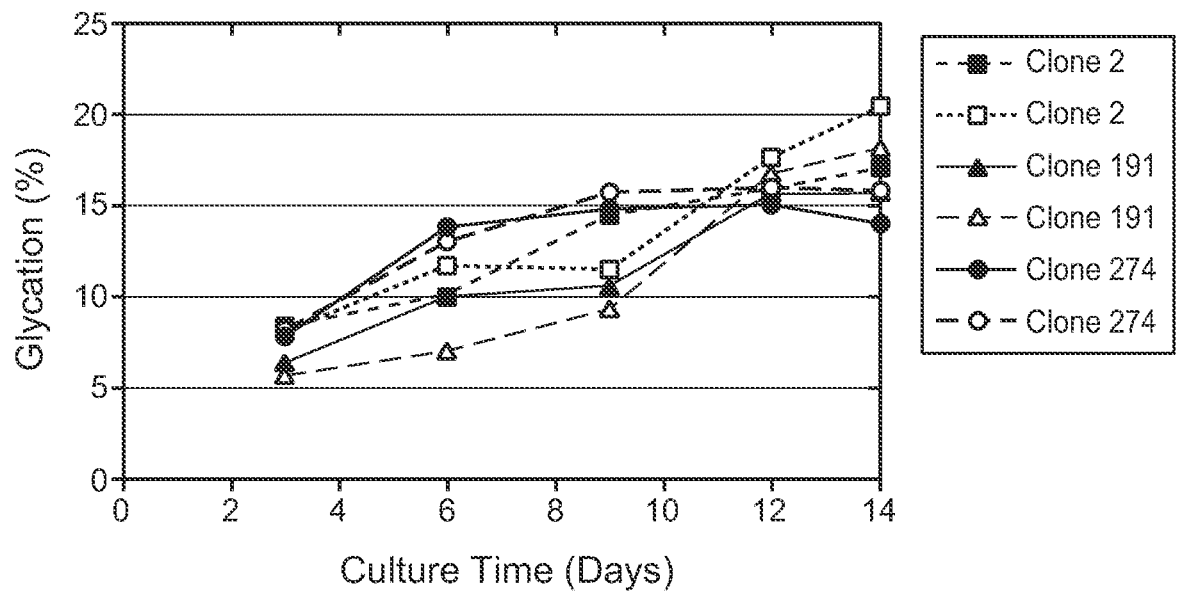
FIGS. 3a and 3b depict antibody glycation and glucose concentration in 2 L bioreactor experiments using a reduced glucose fed batch cell culture method.
Figure 3B:
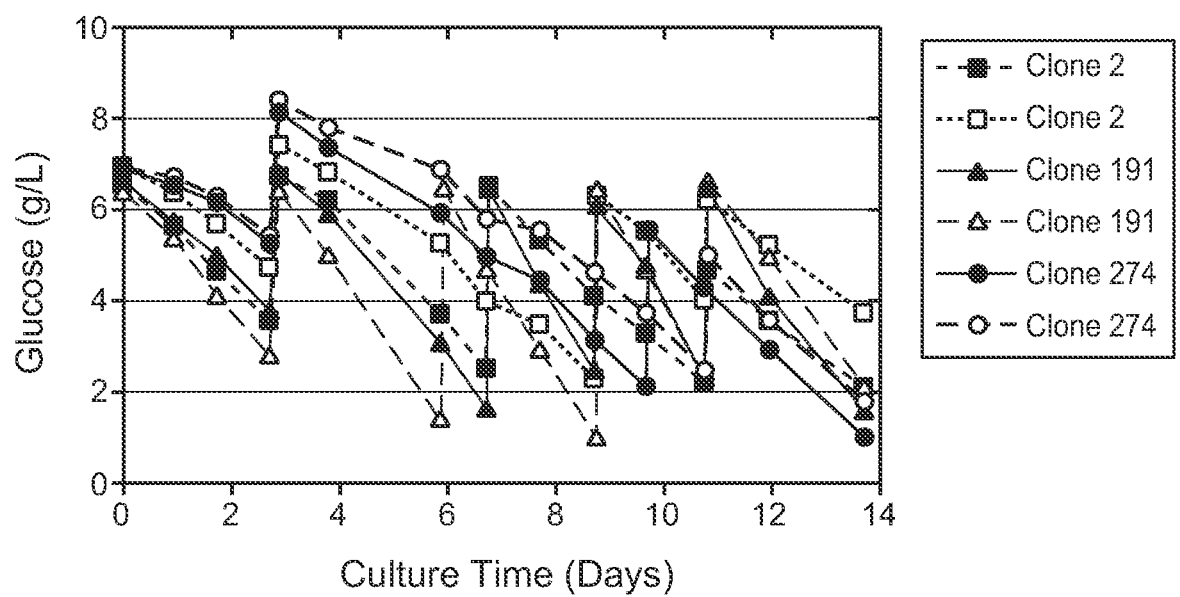

In this set of 2 L experiments, the glucose concentration in the batch feed (nutrients plus glucose) was reduced from the control culture method of approximately 60 g/L to approximately 20 g/L. In addition, when the glucose concentration during the course of culture dropped below 3 g/L, approximately 3 g/L of glucose (without nutrients) was added back to the bioreactor cultures. Therefore, compared to the 40 L bioreactor control experiments (Table 2) and the 2 L control experiments (FIG. 2), the glucose concentration in the batch feed was approximately 67% lower, and the amount of supplemental glucose added was approximately 50% lower in the 2 L experiments, the results of which are shown in FIG. 3. These modifications lowered antibody glycation to 14-20% in the fed batch culture experiments for each of the three stably-expressing clones tested in duplicate bioreactors (see FIG. 3) and showed that glycation can be lowered by reducing the glucose in the culture process. In subsequent 2 L bioreactor experiments, this reduced glucose fed batch cell culture method (also referred to herein as the "fed batch culture method" or "fed batch method") was tested for reproducibility and and clone 2 was used exclusively.

Example 6

Figure 4:
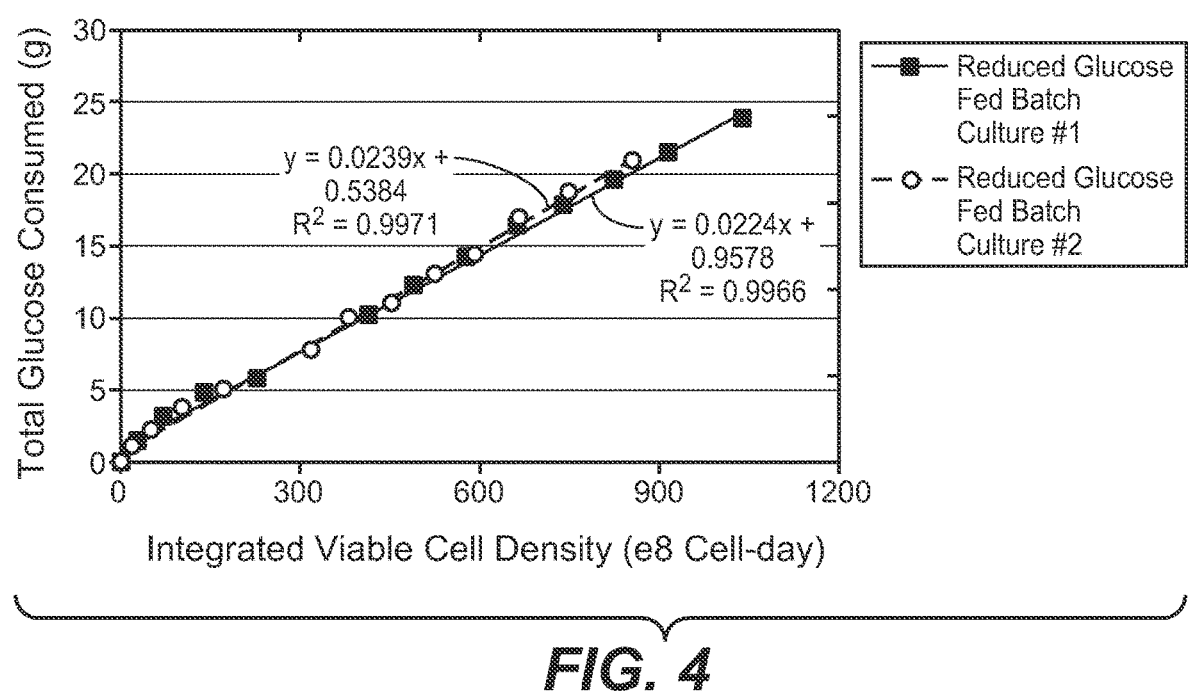
FIG. 4 is a graph of total glucose consumed versus integrated viable cell density for determination of cell-specific glucose uptake rate for clone 2 in 2 L bioreactor reduced glucose fed batch culture experiments.

Determination of Cell-Specific Glucose Uptake Rate for Development of Continuous Feed Methods The cell counts and glucose concentration measurements generated by the duplicate clone 2 cultures in the 2 L bioreactor experiment in Example 5 were used to determine the cell-specific glucose uptake rate for this cell line. The slope of the graph obtained by plotting the total glucose consumed versus the total integrated viable cell density represents the cell-specific glucose uptake rate (FIG. 4). Based on the slopes in FIG. 4, the cell-specific glucose uptake rate was 0.0224 g/e8 cell-day in the first bioreactor, and 0.0239 g/e8 cell-day in the second bioreactor. Taking the average of these 2 measurements, the cell-specific glucose uptake rate for clone 2 was determined to be 0.0231 g/e8 cell-day. This cell-specific glucose uptake rate is used to determine the predicted daily glucose consumption by a bioreactor culture.

To maintain a constant glucose level in the bioreactor, the total amount of glucose to be provided to the cells in culture for the next 24 hours was calculated as a product of the cell-specific glucose uptake rate and the total number of cells in the bioreactor. The total number of cells in the bioreactor was calculated as the product of the daily measured viable cell density and bioreactor volume. The glucose pump for each bioreactor was calibrated and the pump setting was adjusted daily to provide the amount of glucose required to maintain glucose concentration at a constant level.

Experiments in 2 L bioreactors tested three different continuous feed methods in duplicate cases: (1) semi continuous glucose feed method, (2) fully continuous glucose feed method, and (3) continuous nutrient feed method. In the semi continuous glucose feed method, the batch feed did not contain any glucose, and when the glucose concentration first dropped below 2 g/L, continuous glucose feed was initiated by turning on the glucose feed pump to maintain glucose at approximately 1-3 g/L. In the fully continuous glucose feed method, the batch feed did not contain any glucose, and continuous glucose feed was initiated from the beginning of the cell culture process by turning on the glucose feed pump to maintain glucose at approximately 1 g/L. In the continuous nutrient feed process, the batch feed contained approximately 60 g/L glucose, and when the glucose concentration first dropped below 4 g/L, continuous nutrient feed was initiated by turning on the nutrient feed pump to add batch feed at a rate such as to maintain glucose concentration at approximately 1-2 g/L. After the initiation of continuous feed in all these continuous feed methods, the glucose or nutrient feed pump rate was adjusted daily after each cell count so as to provide the projected glucose needs of the culture for the next 24 hours. The glucose or nutrient feed pump was typically stopped approximately 24 hours prior to harvesting the culture.

Example 7

Glycation is Lowered Using Semi Continuous Glucose Feed Method

Figure 5A:
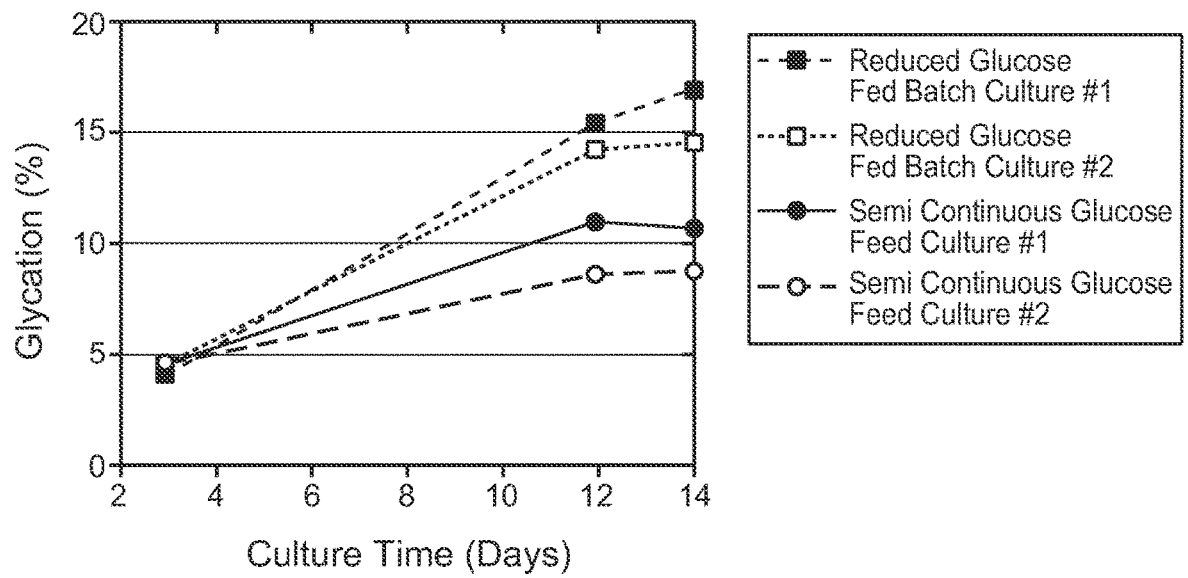
FIGS. 5a and 5b depict antibody glycation and glucose concentration in 2 L bioreactor experiments testing the semi continuous glucose feed method.
Figure 5B:
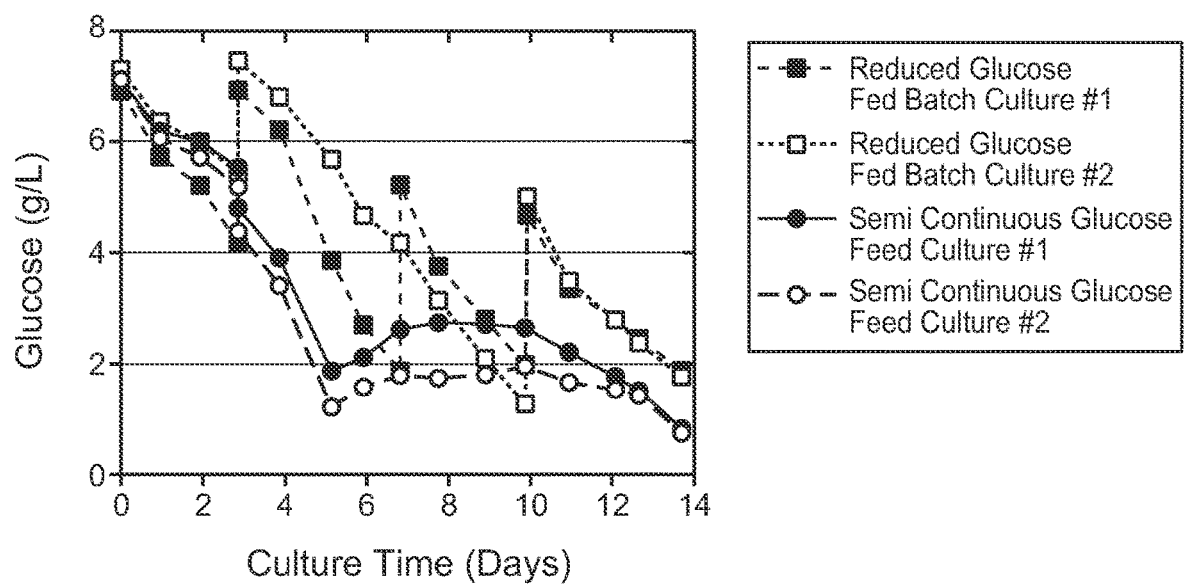

In this set of 2 L bioreactor experiments, duplicate cultures of clone 2 were run using the reduced glucose fed batch culture method (as described in Example 5 herein) and the semi continuous glucose feed method (as described in Example 6 herein). At the time of harvest (Day 14), the fed batch cultures showed antibody glycation of approximately 14-16%, whereas the semi continuous glucose feed cultures showed antibody glycation of approximately 9-11% (FIG. 5a). The glucose concentrations measured were typically lower in the semi continuous glucose feed cultures than in the fed batch cultures (FIG. 5b). These results show that glycation can be lowered by reducing the cell culture glucose concentration.

Example 8

Glycation is Further Lowered Using Fully Continuous Glucose Feed Method

Figure 6A:
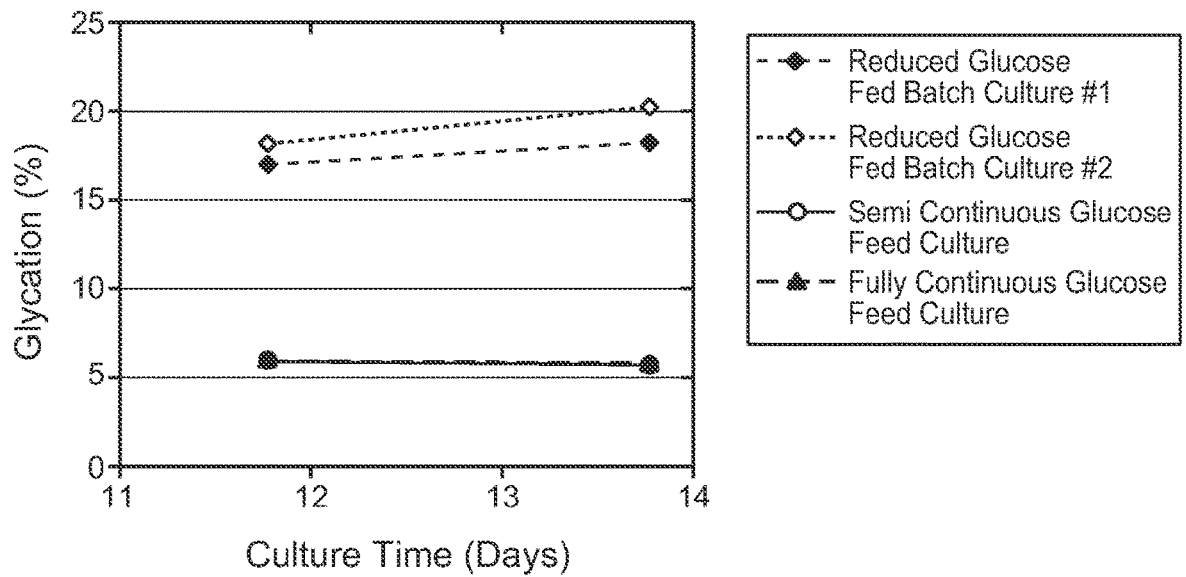
FIGS. 6a and 6b depict antibody glycation and glucose concentration in 2 L bioreactor experiments testing the semi continuous glucose feed and the fully continuous glucose feed methods.
Figure 6B:
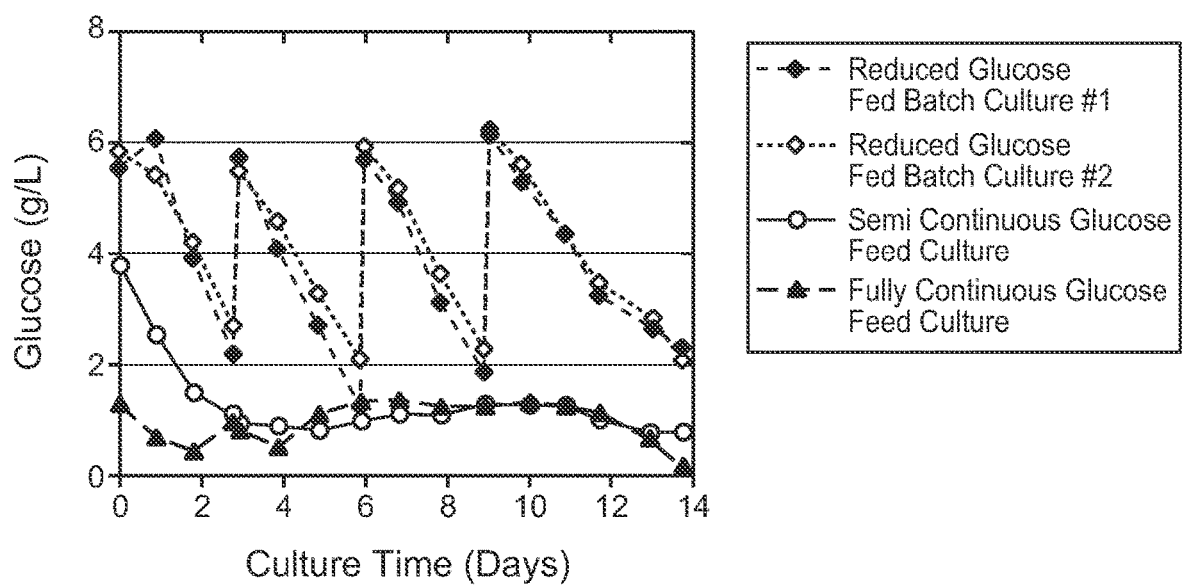

In this set of 2 L bioreactor experiments, cultures of clone 2 were run in duplicate using the reduced glucose fed batch culture method (as described in Example 5 herein) and in singlicates using the semi continuous glucose feed method (as described in Example 6 herein) and the fully continuous glucose feed method (as described in Example 6 herein). At the time of harvest (Day 14), the fed batch cultures contained about 17-20% glycated antibody, whereas the continuous glucose feed cultures contained about 6% glycated antibody (FIG. 6a) and lower average glucose concentrations (FIG. 6b), showing that glycation is lowered by reducing the glucose concentration.

Example 9

Glycation can Also be Lowered Using Continuous Nutrient Feed Method

Figure 7A:
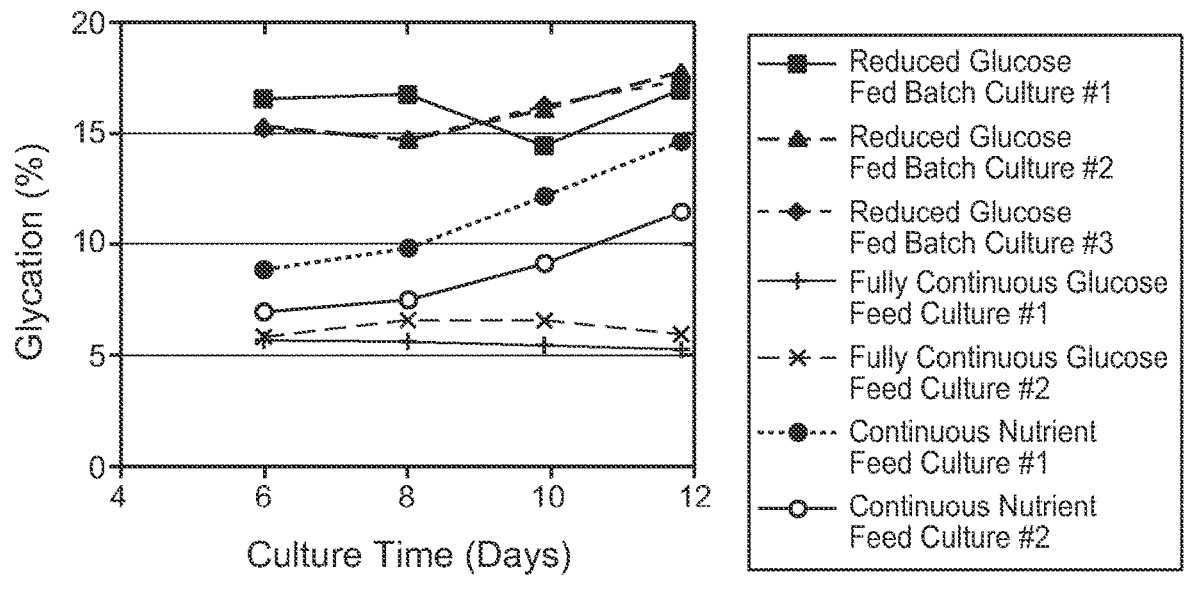
FIGS. 7a and 7b depict antibody glycation and glucose concentration in 2 L bioreactor experiments testing the fully continuous glucose feed method and the continuous nutrient feed method.
Figure 7B:
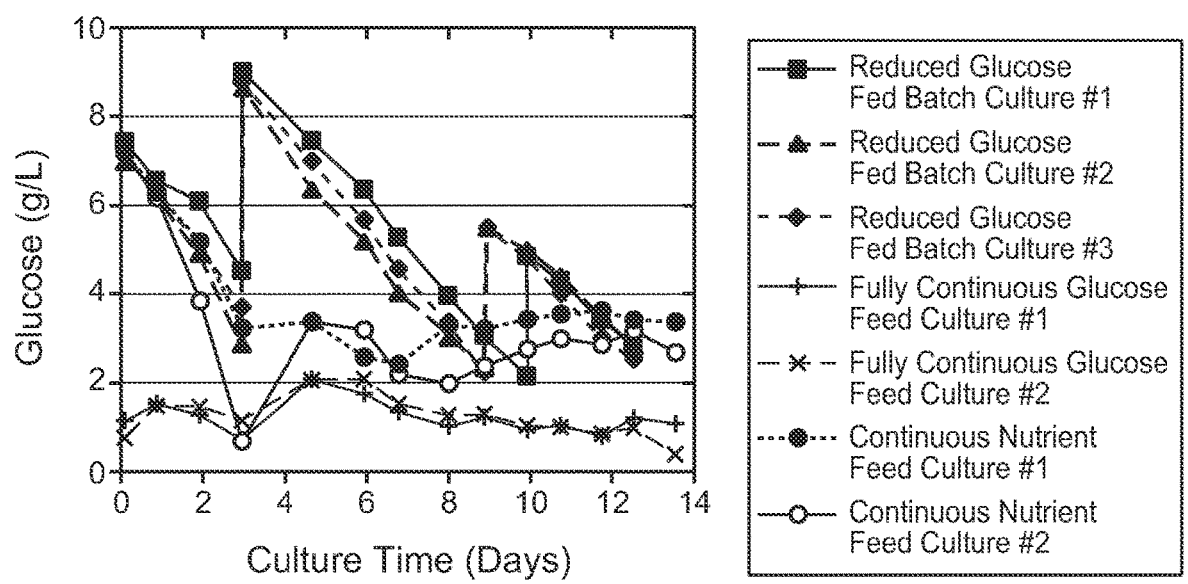

In this set of 2 L bioreactor experiments, cultures of clone 2 were run in triplicate using the reduced glucose fed batch culture method (as described in Example 5 herein), and in duplicates using the fully continuous glucose feed method (as described in Example 6 herein), and the continuous nutrient feed method (as described in Example 6 herein). At the time of harvest (Day 12), the fed batch, fully continuous glucose feed, and continuous batch feed cultures contained approximately 17-18%, 5-6%, and 11-15% glycated antibody, respectively (FIG. 7a). This experiment demonstrated the successful use of the continuous batch feed method to reduce glycation and also showed that cultures with the lower glucose concentrations (FIG. 7b) yielded lower antibody glycation (FIG. 7a).

This invention shows that the percentage of glycated antibody can be reduced by lowering the glucose concentration in the culture medium. The extent to which glucose concentration in the cultures was controlled directly impacted the antibody glycation level (FIGS. 5, 6, and 7). This method of lowering glycation by lowering the concentration of reducing sugar(s) in the cell culture medium is applicable to all secreted proteins.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method of producing a polypeptide with reduced glycation comprising:
   (a) culturing host cells expressing the polypeptide in a cell growth phase,
   (b) thereafter culturing the cells in a polypeptide production phase in a cell culture medium comprising at least one reducing sugar in which the total reducing sugar concentration is maintained between about 0.5 g/L and about 5 g/L by perfusion cell culturing with continus reducing sugar feed or continus nutrient feed comprising at least one reducing sugar, reducing sugar feed or continuous nutrient feed comprising at least one reducing sugar,
   (c) thereafter maintaining the cells in a cell culture medium without further addition of a reducing sugar for from about 24 hours to about 72 hours, and
   (d) thereafter harvesting the polypeptide from the cell culture,
   wherein the polypeptide is an antibody or an antigen binding fragment thereof.

2. The method of claim 1, wherein the total reducing sugar concentration is maintained between about 0.5 g/L and about 4 g/L.

3. The method of claim 1, wherein the total reducing sugar concentration is maintained between about 0.5 g/L and about 3 g/L.

4. The method of claim 1, wherein the total reducing sugar concentration is maintained between about 0.5 g/L and about 2 g/L.

5. The method of claim 1, wherein the total reducing sugar concentration is maintained between about 0.5 g/L and about 1 g/L.

6. The method of claim 1, wherein the method further comprises contacting the host cells with a medium lacking reducing sugar before the culturing of the host cells expressing the polypeptide.

7. The method of claim 1, wherein the method further comprises contacting the host cells with a medium lacking reducing sugar before the culturing of the host cells expressing the polypeptide.

8. The method of claim 1, wherein glycation of the polypeptide is 60% or less of the glycation of the polypeptide produced by a control method.

9. The method of claim 1, wherein glycation of the glycation-susceptible polypeptide is 40% or less of the glycation of the polypeptide produced by a control method.

10. The method of claim 1, wherein glycation of the polypeptide is 20% or less of the glycation of the polypeptide produced by a control method.

11. The method of claim 1, wherein glycation of the polypeptide is 10% or less of the glycation of the polypeptide produced by a control method.

12. The method of claim 1, wherein glycation of the polypeptide is 5% or less of the glycation of the polypeptide produced by a control method.

13. The method of claim 1, wherein the antibody is a bispecific antibody, or an antigen binding fragment thereof.

14. The method of claim 1, wherein the host cell is a mammalian cell.

15. The method of claim 1, wherein the mammalian cell is a Chinese Hamster Ovary (CHO) cell.

16. The method of claim 1, wherein the reducing sugar is glucose.

17. The method of claim 1, wherein glycation of the polypeptide is about 12% to about 44% of the glycation of the polypeptide produced by a control method.

18. The method of claim 1, wherein glycation of the polypeptide is 70% or less of the glycation of the polypeptide produced by a control method.

19. The method of claim 1, wherein c) comprises maintaining the cells in the cell culture medium without further addition of the reducing sugar for from about 24 hours to about 48 hours.

20. The method of claim 1, wherein c) comprises maintaining the cells in the cell culture medium without further addition of the reducing sugar for from about 24 hours to about 36 hours.

* * * * *

SEQUENCE LISTING

<160> NUMBER OF SEQ ID NOS: 15

<210> SEQ ID NO 1

```
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Arg Ala Ser Glu Ser Val Asp Thr Tyr Leu His
1               5                   10

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Lys Tyr Ala Ser Gln Ser Ile Ser
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln Gly Asn Ser Leu Pro Asn Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Phe Ile Thr Asn Asn Tyr Trp Gly
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Ile Ser Tyr Ser Gly Ser Thr Ser Tyr Asn Pro Ser Leu Lys
1               5                   10                  15

Ser

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 6

Met Thr Gly Ser Ser Gly Tyr Phe Asp Phe
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Ala Ser Glu Ser Val Asp Ser Leu Leu His
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Ser Glu Ser Val Asp Thr Leu Leu His
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Ser Glu Ser Val Asp Asp Leu Leu His
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Met Thr Gly Ser Ser Gly Tyr Phe Asp Phe
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ala Arg Thr Gly Ser Ser Gly Tyr Phe Asp Phe
1               5                   10

<210> SEQ ID NO 12
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 12

Ala Gln Thr Gly Ser Ser Gly Tyr Phe Asp Phe
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Thr Gly Ser Ser Gly Tyr Phe Asp Phe
1               5                   10

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Tyr Ala Ser Gln Ser Ile Ser
1               5

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: UNSURE
<222> LOCATION: (1)..(1)
<223> OTHER INFORMATION: Unknown amino acid

<400> SEQUENCE: 15

Xaa Tyr Ala Ser Gln Ser Ile Ser
1               5
```